US00PP34879P2

(12) United States Plant Patent
Grauke et al.

(10) Patent No.: US PP34,879 P2
(45) Date of Patent: Jan. 3, 2023

(54) PECAN TREE NAMED 'ZUNI'

(50) Latin Name: *Carya illinoinensis*
Varietal Denomination: Zuni

(71) Applicant: The United States of America, as represented by the Secretary of Agriculture, Washington, DC (US)

(72) Inventors: Larry J. Grauke, College Station, TX (US); Tommy E. Thompson, College Station, TX (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/668,127

(22) Filed: Feb. 9, 2022

(51) Int. Cl.
*A01H 5/08* (2018.01)
*A01H 6/00* (2018.01)

(52) U.S. Cl.
USPC ..... Plt./153
CPC ..... *A01H 6/00* (2018.05)

(58) Field of Classification Search
USPC ..... Plt./153
CPC ..... A01H 5/0825
See application file for complete search history.

*Primary Examiner* — Kent L Bell
(74) *Attorney, Agent, or Firm* — John Fado; Ariel Atkinson

(57) ABSTRACT

A new and distinct variety of pecan tree, denominated 'Zuni', having large nuts in medium-sized clusters, well-filled cream-colored kernels, medium precocity, and high resistance to scab fungus (*Venturia effusa*).

7 Drawing Sheets

Latin name of the genus and species of the plant claimed: 'Zuni' is a pecan tree that is a *Carya illinoinensis*.

Variety denomination: The new pecan tree is of the variety denominated 'Zuni'.

BACKGROUND OF THE NEW PLANT

'Zuni', tested as 1996-01-0295, is a progeny of a 1996 cross between the 'Pawnee' (seed parent) and 'Waco' (unpatented), (pollen parent) pecan cultivars in Burleson County, Tex. The seedling was grown in Somerville, Tex. and was selected for further testing due to its high nut quality and early nut maturity. 'Zuni' has been evaluated most extensively in orchards in Brownwood, Tex. in a test that comprised 49 selections with 3 control varieties ('Wichita', 'Pawnee', and 'Kanza') (all unpatented). All trees in this block had between 5 to 6 replicate grafted clones.

SUMMARY OF THE INVENTION

'Zuni' is distinguished from other pecan varieties due to the following unique combination of characteristics: large nuts in medium-sized clusters, well-filled cream-colored kernels, medium precocity, and high resistance to scab fungus (*Venturia effusa*). However, 'Zuni' has only been monitored in Central Texas and has not been observed under all environmental conditions and cultural practices. Therefore, some characteristics may differ outside of Central Texas or with different management practices.

BRIEF DESCRIPTION OF THE FIGURES

The accompanying drawings include color photographs that are as nearly true as it is reasonably possible to make in a color illustration of this type.

Figure 1:
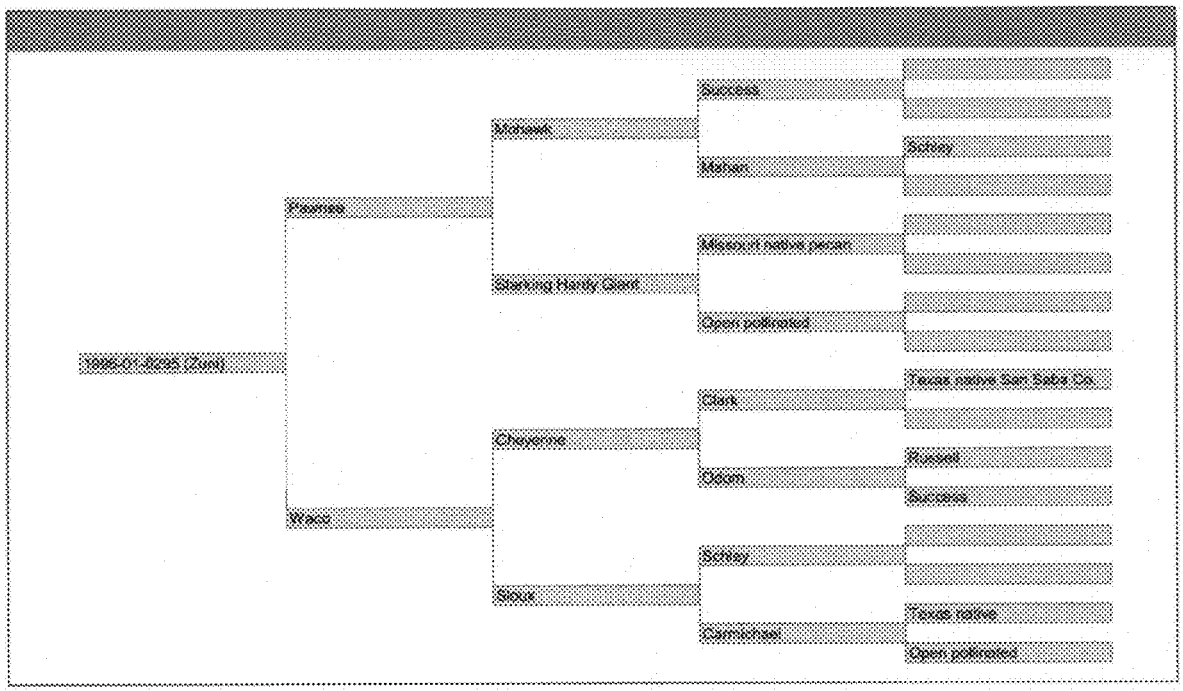
FIG. 1 is a chart showing the pedigree of 'Zuni'.
Figure 2:
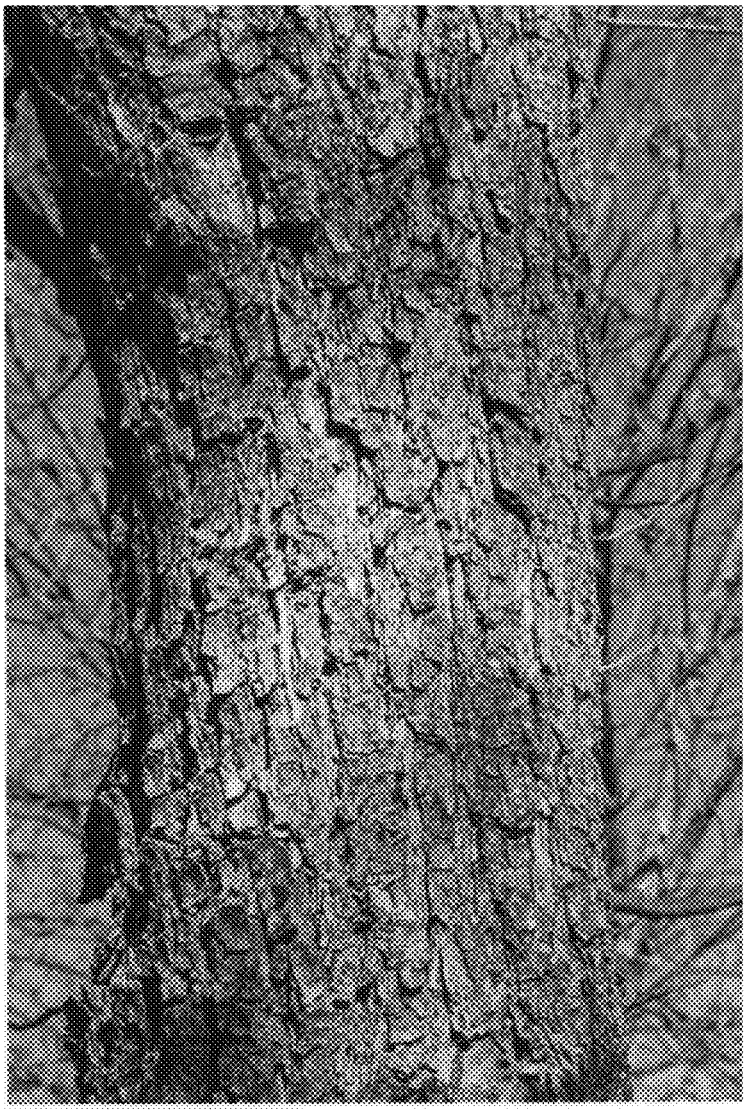
FIG. 2 is a photograph showing the scaly bark texture of 'Zuni' at 15 years after grafting. Photo taken in Brownwood, Tex. on Apr. 7, 2021.

Due to photographical light, chemical development, processing and printing, the leaves and fruit depicted in these photographs may or may not be accurate when compared to the actual botanical specimen.

DETAILED BOTANICAL DESCRIPTION

All color descriptions are based on of the Munsell Plant Tissue Color Book: 2012 Year Revision (2019 Printing).

The botanical description below is based on six grafted clones of 'Zuni' located in the same orchard in Brownwood, Tex. In addition, the ortet for 'Zuni' is grafted into the canopy of two trees in Burleson County, Tex. Unless otherwise noted, the observations below were collected from April-June in 2021 (15 years after grafting).

Parentage:

*Seed parent.*—'Pawnee'.

*Pollen parent.*—'Waco'.

Tree:

a. *Overall shape*.—General shape and height to width ratio: average 1.46. Tree shape is upright with a narrow canopy.

b. *Vigor*.—Vigorous. 'Zuni' was partially fruiting 2 years after grafting. A full crop load started 3 years after grafting.

c. *Height*.—Average Height: 13.66 m.

d. *Width/trunk diameter*.—i. Canopy Width: 9.52 m. ii. Trunk Diameter: 302 mm.

e. *Trunk bark texture*.—Scaly when Mature.

f. *Trunk bark color*.—Grey-Brown — 2.5Y 5/2.

g. *Branch color*.—i. Woody stage branch shoots: Grey-Brown — 2.5Y 5/2. ii. Lenticels: Lenticel shape is highly variable. An average length would be 1.44 mm. The average width would be 1.12 mm. iii. Lenticel Color: Dark Peach — 7.5YR 7/6.

h. *Internodes*.—The average length between the $3^{rd}$ and $4^{th}$ leaf from the base of the shoot is 18.11 mm.

i. *Disease and insect resistance*.—i. Pecan Scab, *Venturia effusa* (leaf and nut), data from 2010-2012, 2015, and 2016 In our unsprayed orchards, 'Zuni' has had only trace amounts of either leaf or nut scab.

j. *Leaves* (*data from June* 2021).—i. Leaf Arrangement and Color. 1. Leaves are odd-pinnately compound opposite. 2. Upper leaf color is Dark Forest Green — 7.5GY 3/4. 3. Lower leaf color is Green — 5GY 4/4. ii. The number of leaves per shoot and the number of leaflets per mature leaf. 1. Leaves per shoot: 6-10, Average 8. 2. Leaflets per leaf: 9-13, Average 11. iii. The angle of leaflet pairs to the rachis: 45°. iv. Leaflet blade: flat and not convoluted. v. Length and width of a mature leaf ($4^{th}$ leaf from the base of the shoot). 1. Length Range: 328-430 mm. Average: 380 mm. 2. Width Range: 277-341 mm. Average: 301 mm. vi. Petiole shape and color. Petiole shape is circular. Petiole color is Green Yellow — 5GY 5/6. vii. Petiole length of the $4^{th}$ leaf from the base. 1. Length Range: 45-81.9 mm. Average: 54.5 mm. 2. Width Range: 1.91-2.26 mm. Average: 2.14 mm. viii. Leaflet size and shape ($4^{th}$ leaflet on $4^{th}$ leaf). 1. Leaflet Size Range: 120-171 mm. Average: 147.8 mm. 2. Width Size Range: 30-46 mm. Average: 37.8 mm. 3. Leaflet shape is falcate with serrate margins, an oblique base, and an acuminate tip. ix. Texture of upper leaf. The leaf texture is smooth on both the upper and lower surfaces with a glossy sheen. x. Sheen: glossy. xi. Petiolule. 1. Petiolule Length Range: 5.24-10.37 mm. Average: 7.15 mm. 2. Petiolule Width Range: 0.79-1.27 mm. Average: 1.0 mm. xii. Margin: Leaf margin is serrate. xiii. Tip Shape: Leaf tip is acuminate. xiv. Pubescence (Upper leaf and Lower leaf) Leaf pubescence is mostly glabrous with occasional pilose regions.

Inflorescence:

a. *General description*.—'Zuni' is monoecious, anemophilous, and protandrous (Table 1).

b. *Flowers*.—i. The number of pistillate flowers and arrangement of the flowers. 1-4 individual pistillate flowers per pedicel spike are borne alternately on terminally positioned spikes. ii. Description of the pistillate flower and pedicels. Mid-to-late pistil receptivity with reflexed, red stigmas. iii. Staminate catkin length and width (in mm). 1. Catkin Length Range: 45-125 mm. Average: 81.82 mm. 2. Catkin Width Range: 5-8 mm. Average: 5.85 mm. iv. Staminate color, pollen color. 1. Staminate color: Golden — 2.5GY 6/10. 2. Pollen color: Yellow — 5Y 8/10. v. Involucre size, including the stigma (length and width). 1. Involucre Length Range: 7.74-9.84 mm. Involucre Length Average: 9.11 mm. 2. Involucre Width Range: 1.42-2.17 mm. Involucre Width Average: 1.82 mm. vi. Description of Anthocyan on stigma. The stigmas are red. vii. Flower pistil color(s). Dominant stigma color is red (5R 3/4). viii. Number and color of bracts, shape (lanceolate), flower length and width, and description of petal fusion and the end resulting flower shape (copular involucre): Three lanceolate bracteoles are present and one bract (all green: 5G 4/8). The bract is slightly longer than the three bracteoles. The bracteoles and bract are fused at the base to form a copular involucre.

Fruit a. *Mature fruit is dehiscent.* b. *Shuck*.—i. Shuck color is green — 7.5GY 6/8.

c. *Fruit split during water stage has not been observed to be a problem.* d. *Shuck decline during kernel formation has not been observed to be a problem.*

Nuts:

a. *Observations are from detailed measurements of five nuts per year from multiple years*.—2009-2018 (except no data in 2013).

b. *Size*.—i. The average nut length is about 40.40 mm. The average nut width is about 22.76 mm. The length-to-width ratio is 1.78. ii. Nut cross-section is laterally compressed with a flatness ratio (width across sutures to the width between sutures) of 1.14.

c. *Form*.—i. The shape of the nut with the shape of the cross-section. The nut is oval elliptic shaped (length to height ratio 1.57) with a round cross section. ii. Base shape: Oblique. iii. Apex shape: Oblique. iv. Presence and locations of defining features: Nut apex is sometimes grooved. v. Description of shell suture: Often elevated. vi. Description of shell surface: Black lines and patches stretch from the apex to the midpoint of the nut, covering up to 50% of the upper nut surface. In addition, black spots may cover the entire shell surface. vii. Description of shell topography: Smooth.

d. *Dorsal grooves*.—Kernels have wide, shallow dorsal grooves that do not trap packing material.

e. *Ventral grooves*.—Kernels have a narrow, shallow ventral groove.

f. *Weight*.—9.53 g.

g. *Cluster size*.—On average 2.32 nuts per cluster.

h. *Shell topography*.—Generally smooth, with a slight ridge on the suture.

i. *Shell thickness*.—0.88 mm average, moderately thick.

j. *Shell solor*.—Brown — 7.5YR 4/4.

k. *Kernel color*.—Light cream — 2.5YR 8/4.

l. *Kernel percentage* 56.23% Average.

m. *Nut maturity date*.—October $3^{rd}$.

COMPARISON TO OTHER VARIETIES

Figure 3:
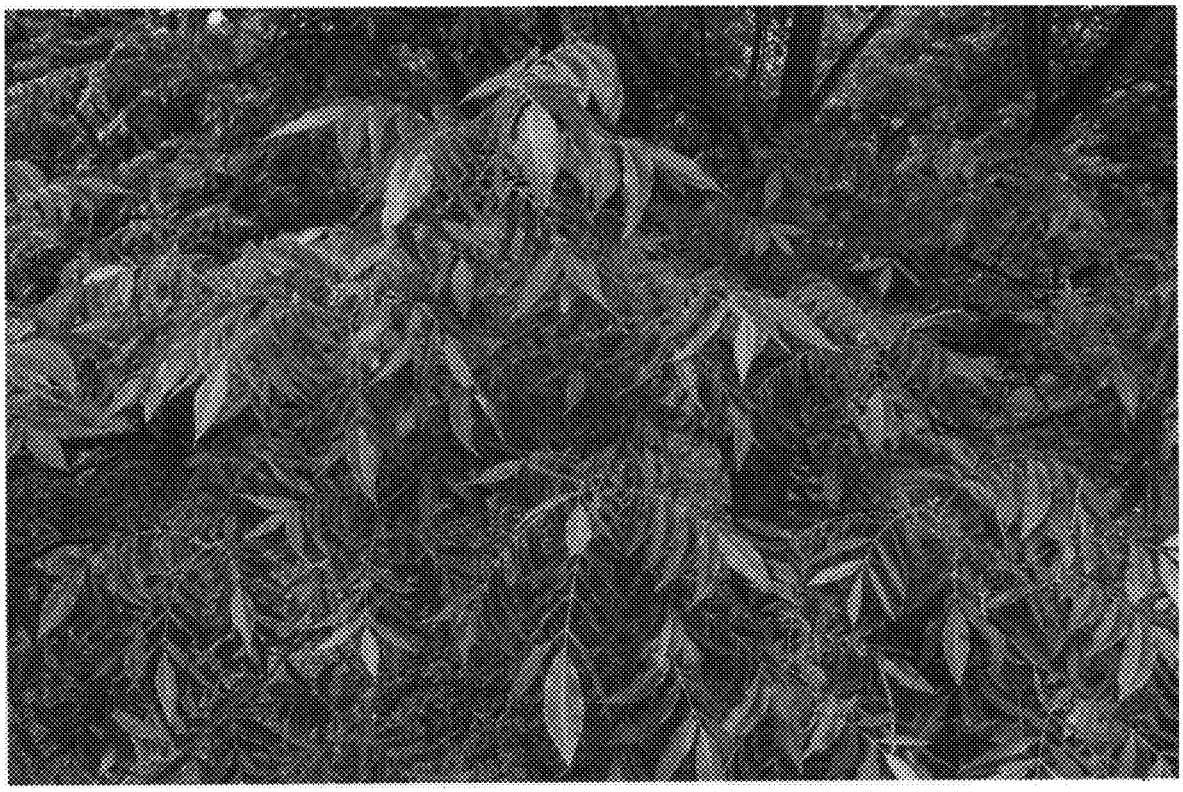
FIG. 3 is a photograph of the leaf architecture of 'Zuni' at 15 years after grafting. Photo taken in Brownwood, Tex. on Jun. 4, 2021.
Figure 4:
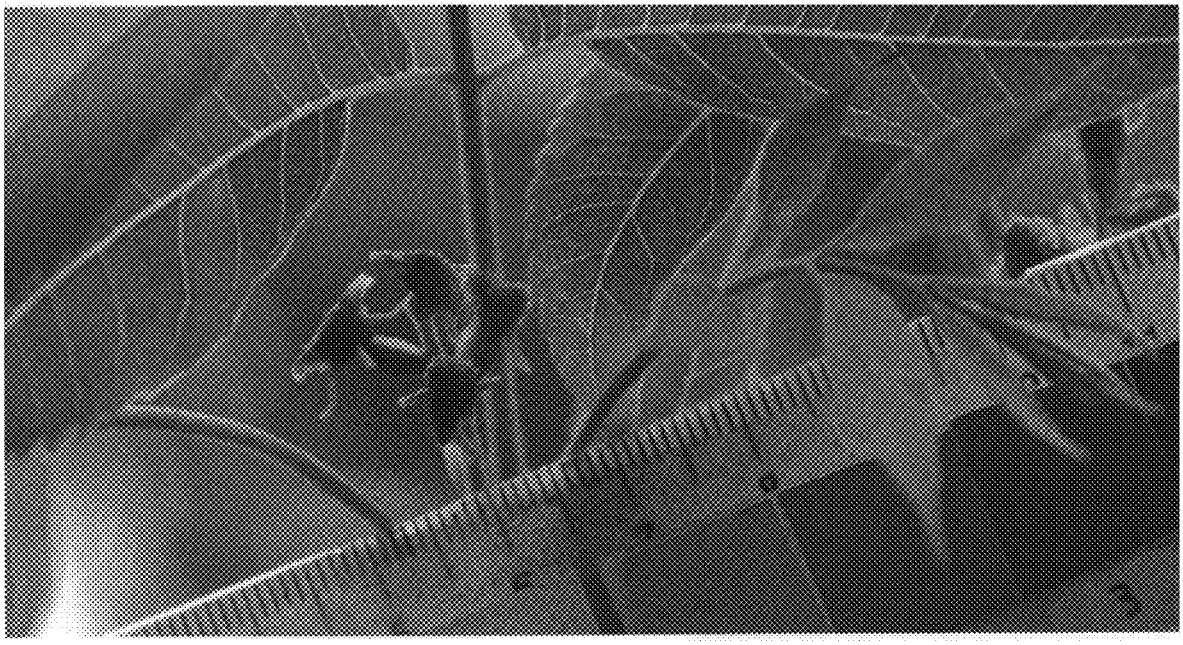
FIG. 4 is a photograph of red, reflexed 'Zuni' pistillate flowers. Photo taken in Brownwood, Tex. on May 13, 2021.

'Zuni' is a new pecan cultivar that is outstanding for producing high-quality pecans with attractive, light cream kernels. 'Zuni has dark forest green leaves comparable to 'Pawnee'. Leaflet orientation is similar to most pecan trees, wherein the opposite leaflet pairs are oriented about 45 degrees from the rachis (FIG. 3).

'Zuni' is protandrous, with blooming patterns comparable to its seed parent 'Pawnee'. It has early to mid-season pollen shed and mid-to-late season pistillate receptivity (Table 1). It usually bears 1-4 alternately-positioned pistillate flowers per pedicel spike. 'Zuni' has pistillate flowers with reflexed, red stigmas, similar to its seed parent 'Pawnee', but contrasting to the green stigmas of its pollen parent 'Waco'. It should be a good pollinizer for and be well pollinized by 'Wichita' and 'Lakota' (unpatented). On average, spring bud break for 'Zuni' was in late March in Brownwood, Tex. (85.9 Julian days). 'Wichita' broke bud a few days earlier (81.8 Julian days), and its seed parent, 'Pawnee', broke bud a few days later (92.3 Julian days) (Table 1). No damage was observed from the prolonged freeze in early February 2021 in Central Texas.

'Zuni' exhibited minimal scab fungus (*Venturia effusa*) susceptibility within our unsprayed orchards in Brownwood, Tex. Both its seed parent 'Pawnee' and pollen parent 'Waco' have moderate-to-severe scab susceptibility. Within our Brownwood orchard from the years 2010-2012 and 2015, 'Pawnee' showed a surprising lack of leaf and nut scab infection, despite nearby 'Wichita' trees showing some infection. 'Zuni' also displayed little to no infection during those years. From 2015-2017, we observed the expected levels of nut scab infection for the known-susceptible varieties in that orchard while 'Zuni' continued to display resistance. The average nut scab observed that period for 'Zuni' was only 1.38 percent on the standard area diagram scale of 1 to 100 percent, comparable to 'Kanza' at 1.42 percent, with 'Pawnee' at 30.89 percent and 'Wichita' at 91.51 percent infection (Table 2); indicating a much greater resistance of 'Zuni' to nut scab fungus than its seed parent 'Pawnee' and another susceptible control variety.

*Neofusicoccum* spp. is a new fungal disease first noticed in 2010, colloquially called "Terminal dieback". It is not usually a severe problem in fungicide-managed orchards. While it has not been rated on 'Zuni', both of its parents 'Pawnee' and 'Waco' are among the most susceptible cultivars in our unsprayed orchards in Burleson County, Tex. It is likely that 'Zuni' will need fungicide management in more humid environments.

Figure 5:
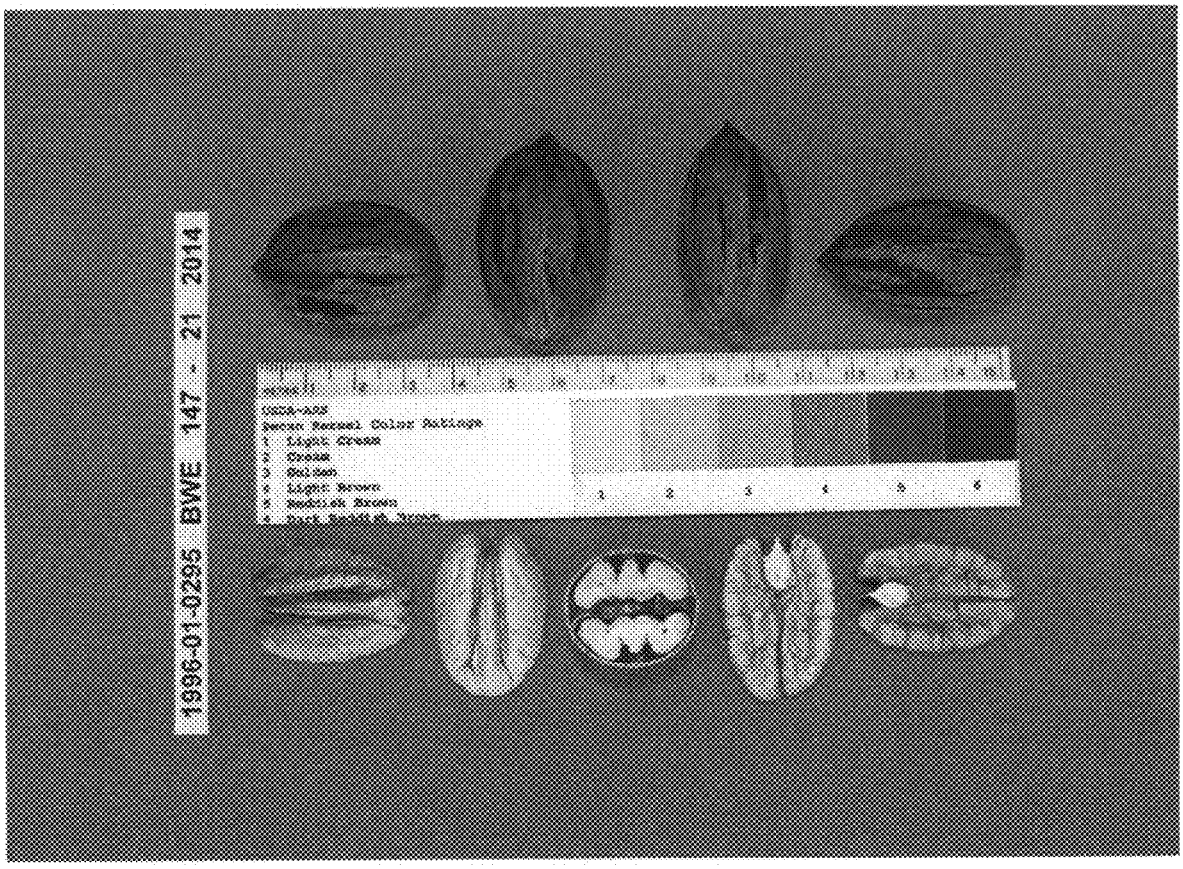
FIG. 5 is a photograph of a nut quality panel of 'Zuni'. Photo taken in Brownwood, Tex. on Nov. 13, 2014.
Figure 6:
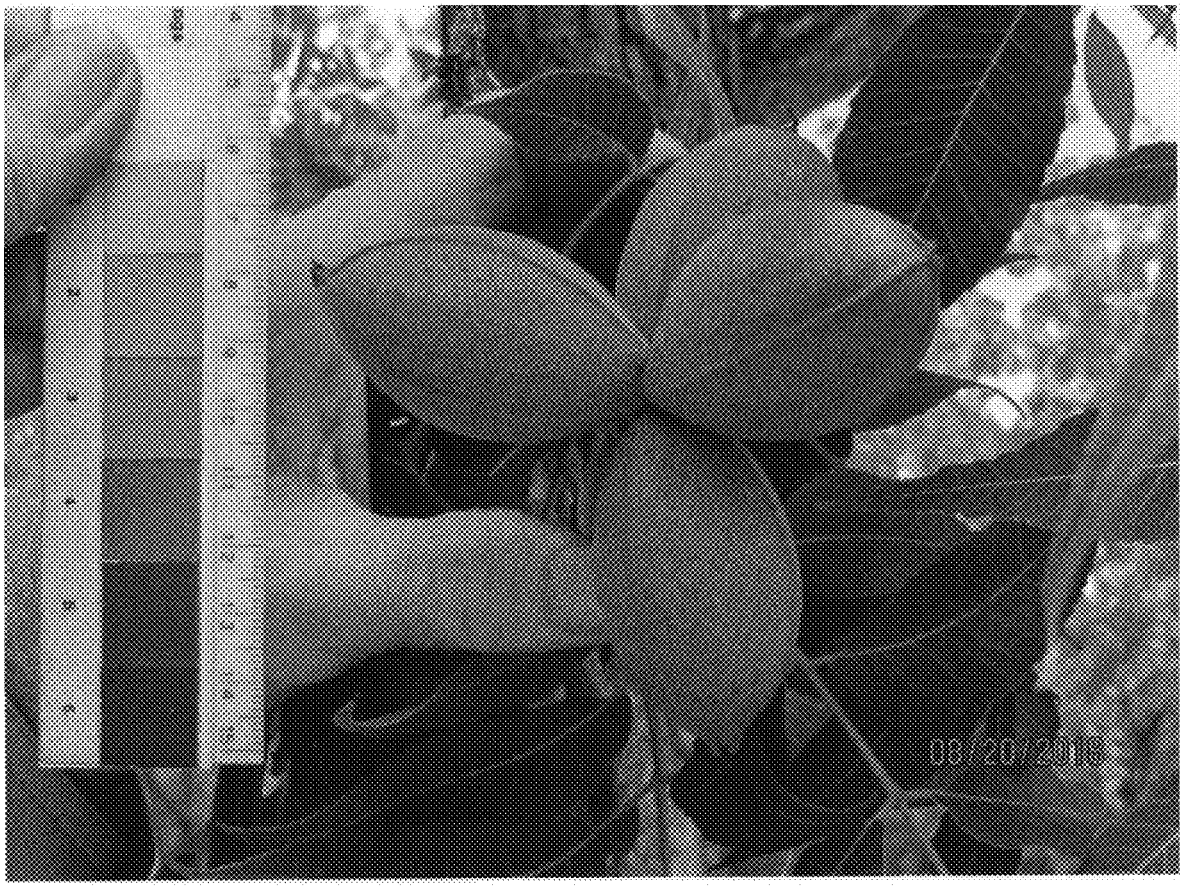
FIG. 6 is a photograph of the nut clusters of 'Zuni'. Photo taken in Brownwood, Tex. on Aug. 20, 2018.
Figure 7:
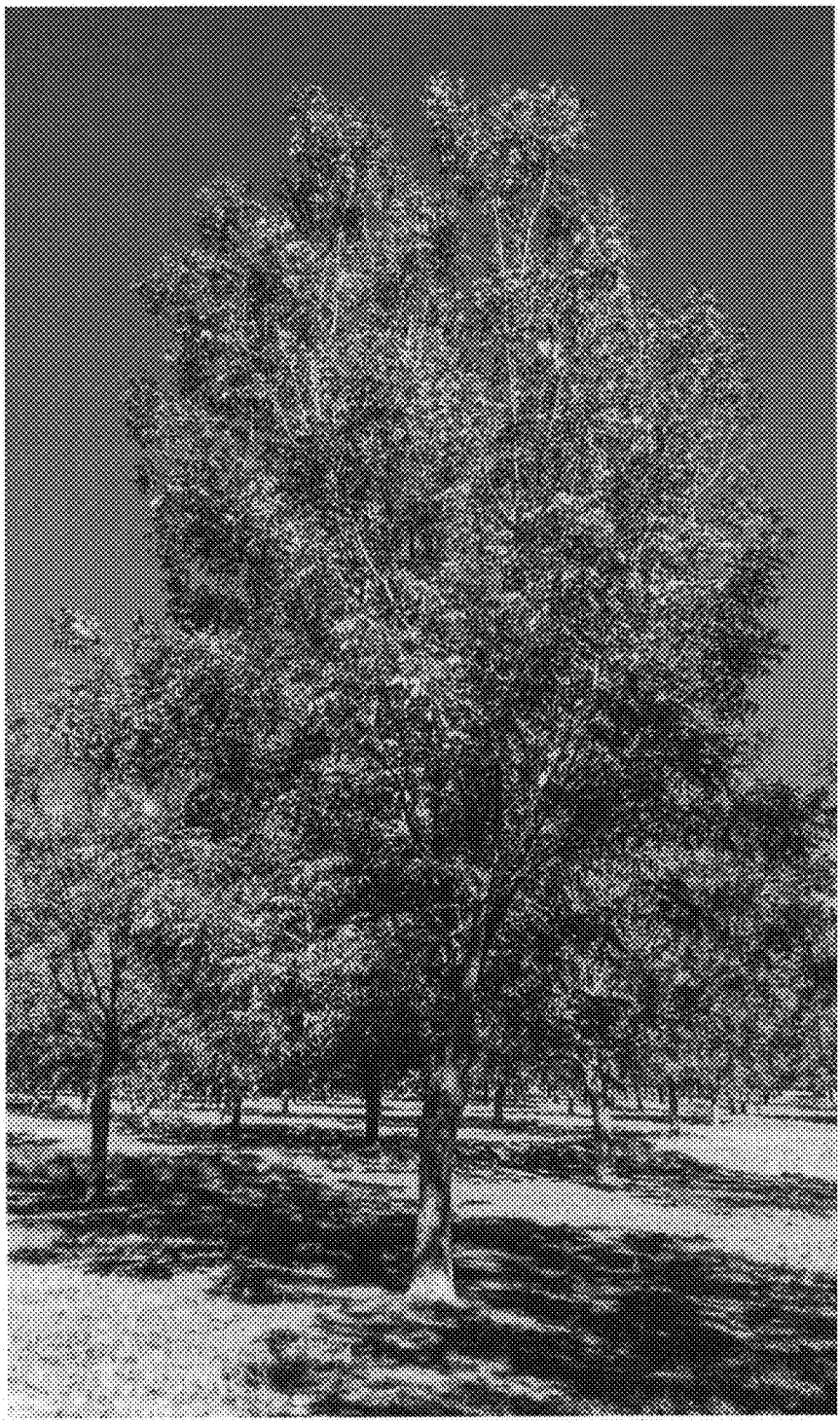
FIG. 7 is a photograph of the canopy structure of a 'Zuni' tree at nine years after grafting on an 'Apache' (unpatented) seedling rootstock. Photo taken in Brownwood, Tex. on Oct. 29, 2015.

'Zuni' has consistently produced large, high-quality nuts that mature early and are ready to harvest in early October in Central Texas. In Brown County, Tex., 'Pawnee' nuts mature in late September, and nuts from the pollen parent 'Waco' mature in mid-October. On average, 'Zuni' nuts mature around October 1$^{st}$ (275.5 Julian days) (Table 3). The average nut weight is 9.53 grams for 'Zuni', compared to 8.52 g for 'Pawnee' and 7.06 for 'Wichita'. The average number of nuts per pound is 47.57 for 'Zuni', compared to 54.63 for 'Pawnee' and 63.85 for 'Wichita. 'Zuni' has, on average, a wider nut than its seed parent 'Pawnee' (22.76 mm vs 21.43 mm). Nut percent kernel averages 56.23 with a light cream color (FIG. 5) compared to its seed parent 'Pawnee', which has an average 59.14 percent kernel with golden kernels in Brownwood, Tex. 'Zuni' averages 2.32 nuts per cluster, compared to 3.28 for 'Pawnee' and 3.31 for 'Wichita' (Table 5). In the 6$^{th}$ leaf year, 'Zuni' bore 17.26 dry weight pounds of nuts, compared to 21.16 for 'Pawnee' and 22.05 for 'Wichita' (Table 4).

Further detailed information is presented in the tables below:

TABLE 1

Bud break, pollen shedding and stigma receptivity of 'Zuni' and other 3 pecan cultivars (control) in the USDA-ARS National Pecan Advanced Clone Testing System (NPACTS) orchard in Brownwood, Texas.

| Cultivar | Dichogamy | Bud Break* | 5$^{th}$ Week April** | 1$^{st}$ Week May | 2$^{nd}$ Week May |
|---|---|---|---|---|---|
| Zuni | Protandrous (type I) | March 27$^{th}$ (85.9 days) C | PS | PS/PR | PR |
| Kanza | Protogynous (type II) | March 31$^{st}$ (89.6 days) B | PR | PR | PS |
| Pawnee | Protandrous (type I) | April 2$^{nd}$ (92.3 days) A | PS | PS | PR |
| Wichita | Protogynous (type II) | March 23$^{rd}$ (81.8 days) D | PR | PR/PS | PS |

Note:
A total of 52 entries (49 breeding lines and 3 cultivars) (grafted onto a rootstock cultivar 'Apache' in 2007) were arranged in the NPACTS orchard with a randomized complete block design in 6 blocks in Brownwood, Texas.
*Bud break was rated using the following scale: 1 = dormant, 2 = swell, 3 = inner scale split, 4 = burst, 5 = first leaflet expansion, 6 = 25% expansion, 7 = to 50% leaf expansion, 8 = to 75% leaf expansion, 9 = fully expanded leaves. Data is the average of three years records (2016, 2017, and 2021). For comparison, Julian days (in bracket) were calculated when bud break scale reached to scale 3.
**PS = Pollen Shedding, PR = Pistillate Receptivity.
Values within column followed by a common letter are not significantly different according to Student's t test at $p < 0.05$.

TABLE 2

Comparison of average leaf and fruit scab susceptibility of 'Zuni' and three cultivars (controls) in the USDA-ARS National Pecan Advanced Clone Testing System (NPACTS) orchard (unsprayed) in Brownwood, Texas.

| Cultivar | Leaf Scab* | Nut Scab* | Nut Scab Percent** |
|---|---|---|---|
| Zuni | 1.00 B | 1.07 B | 1.38 C |
| Kanza | 1.00 B | 1.04 B | 1.42 C |
| Pawnee | 1.00 B | 1.42 B | 30.89 B |
| Wichita | 2.71 A | 3.49 A | 91.51 A |

*measured with Hunter-Roberts Scale, 1 = no scab, 5 = greater than 50% coverage of leaves or fruit with scab lesions. Data are four years' average (2010-2012 and 2015).
**measured with standard area diagram scale (% of nut with scab lesions) across three years (2015-2017).
Values within column followed by a common letter are not significantly different according to Student's t test at $p < 0.05$.

TABLE 3

Comparison of average nut characteristics (Wt./nut [g], Nuts/lbs. [no.], Nut length [mm], Nut Length/width, Nut flatness [ratio of nut width across suture to between suture], Kernel [percentage], Nut Maturity Date [75% shuck dehiscence] of five nuts per tree for four cultivars in Brownwood, TX from 2009-2018. Nut sampling was incomplete in 2013.

| Cultivar | Nut Length mm | Nut Height mm | Nut Width mm | Nut Weight gm | Kernel Percent |
|---|---|---|---|---|---|
| Zuni | 40.40 A | 25.76 A | 22.76 A | 9.53 A | 56.23 B |
| Kanza | 34.58 B | 22.92 C | 21.71 BC | 6.61 D | 52.83 C |
| Pawnee | 41.06 A | 23.79 B | 21.43 C | 8.52 B | 59.14A |
| Wichita | 41.23 A | 21.18 D | 21.97 B | 7.06 C | 55.58 B |

| Cultivar | Nuts Per Lb. | 75% Shuck Split (Julian Days) | Nut Height to Width Ratio |
|---|---|---|---|
| Zuni | 47.57 C | Oct. 3rd (275.53) B | 1.13 |
| Kanza | 69.48 A | Sep. 28th (270.54) C | 1.06 |
| Pawnee | 54.63 B | Sep. 24th (267.01) D | 1.11 |
| Wichita | 67.19A | Oct. 20th (292.74) A | 0.96 |

Values within column followed by a common letter are not significantly different according to Student's t test at $p < 0.05$.

TABLE 4

Comparison of Dry Weight Nut Yield (average lbs./tree) of five to six replicates of four cultivars growing in one orchard in Brownwood, Texas from 2009-2012. Precocity (years to initial fruiting after nursery transplant) can also be interpreted from this data. These trees were grafted in 2007.

| Cultivar | Yr. 3 2009 | Yr. 4 2010 | Yr. 5 2011 | Yr. 6 2012 | ABI* |
|---|---|---|---|---|---|
| Zuni | 0.07 | 0.60 | 0.62 | 17.26 | 0.57 |
| Kanza | 0.07 | 0.75 | 0.44 | 8.26 | 0.66 |
| Pawnee | 0.18 | 0.46 | 0.18 | 21.16 | 0.62 |
| Wichita | 0.04 | 0.55 | 2.09 | 22.05 | 0.76 |

*The alternate bearing index (ABI) is a measure of a cultivars tendency to produce alternating high and low yields. Ranges are from 0 .to 1, with 0 = no alternation and 1= complete alternation (Pearce and Dobersek-Urbanc, 1967). 1)) /(a(n) + a(n − 1)) ABI = 1/(n − 1) X. {|(a2 − a1)/(a2 + a1) + (a3 − a2)/(a3 + a2) . . . + |(an) − a(n − } where n = number of years, and a1, a2, . . . , a(n − 1), an = yield of corresponding years.
Values within column followed by a common letter are not significantly different according to Student's t test at $p < 0.05$.

TABLE 5

Comparison of Average Nut Cluster Size (Nuts/Cluster [no.]) of five to six replicates of four cultivars at Brownwood, Texas from 2009-2017)

| Cultivar | Yr. 3 2009 | Yr. 4 2010 | Yr. 5 2011 | Yr. 6 2012 | Yr. 8 2014 | Yr. 10 2016 | Yr. 11 2017 | Average |
|---|---|---|---|---|---|---|---|---|
| Zuni | 2.55 | 2.26 | 1.97 | 3.31 | 2.73 | 4.33 | 2.04 | 2.32 C |
| Kanza | 1.47 | 2.56 | 2.33 | 3.23 | 2.93 | 4.02 | 3.02 | 2.99 B |
| Pawnee | — | 2.30 | 1.94 | 3.93 | 2.68 | 4.83 | 2.67 | 3.28 AB |
| Wichita | 2.00 | 3.23 | 2.80 | 3.88 | 3.10 | 4.33 | 3.22 | 3.31 A |

Note: No nuts were harvested in 2013 and 2015.
Values within column followed by a common letter are not significantly different according to Student's t test at $p < 0.05$.

We claim:

1. A new and distinct variety of pecan tree named 'Zuni' as illustrated and described herein.

* * * * *